(12) United States Patent
Tae et al.

(10) Patent No.: US 10,052,283 B2
(45) Date of Patent: Aug. 21, 2018

(54) COMPOSITION FOR FORMING PLURONIC-BASED HYDROGEL WITH IMPROVED STABILITY

(71) Applicant: Gwangju Institute of Science and Technology, Gwangju (KR)

(72) Inventors: Giyoong Tae, Gwangju (KR); Da-ae Won, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 14/625,686

(22) Filed: Feb. 19, 2015

(65) Prior Publication Data

US 2015/0231246 A1 Aug. 20, 2015

Related U.S. Application Data

(60) Provisional application No. 61/942,234, filed on Feb. 20, 2014.

(30) Foreign Application Priority Data

May 29, 2014 (KR) ........................ 10-2014-0064945

(51) Int. Cl.
| | | |
|---|---|---|
| A61K 47/10 | (2017.01) | |
| A61K 47/06 | (2006.01) | |
| A61K 9/00 | (2006.01) | |
| A61K 38/18 | (2006.01) | |
| A61K 9/06 | (2006.01) | |

(52) U.S. Cl.
CPC .............. *A61K 9/06* (2013.01); *A61K 9/0024* (2013.01); *A61K 38/1866* (2013.01); *A61K 47/06* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 2005/0147684 A1* | 7/2005 | Rosenthal | ............ | A61K 9/0024 424/486 |
| 2011/0008441 A1* | 1/2011 | Chu | ........................ | C08G 69/10 424/486 |
| 2013/0230496 A1* | 9/2013 | Mohapatra | ............ | A61K 47/36 424/93.7 |

FOREIGN PATENT DOCUMENTS

| | | | |
|---|---|---|---|
| KR | 1020130115459 A | | 10/2013 |
| WO | WO 2012028881 A1 | * | 3/2012 |

OTHER PUBLICATIONS

M.R. Kim et al., "Temperature-responsive and degradable hyaluronic acid/Pluronic composite hydrogels for controlled release of human growth hormone," Journal of Controlled Release 80 (2002) 69-77.*
Sigma-Aldrich, "Pluronic® F-127," <http://www.sigmaaldrich.com/catalog/product/sigma/p2443?lang=en&region=US>, Copyright 2015, p. 1-5.*
X. Ma et al., "Temperature-sensitive poly(N-isopropylacrylamide)/ graphene oxide nanocomposite hydrogels by in situ polymerization with improved swelling capability and mechanical behavior," European Polymer Journal 49 (2013) 389-396 (Available online Nov. 23, 2012).*
A. Sahu et al., "A stimuli-sensitive injectable graphene oxide composite hydrogel," Chem. Commun., 2012, 48, 5820-5822.*
Tina Vermonden et al., Photopolymerized Thermosensitive Hydrogels: Synthesis, Degradation, and Cytocompatibility, 2008, pp. 919-926, vol. 9, Biomacromolecules, American Chemical Society.
Kyung Jae Jeong et al., Interplay between Covalent and Physical Interactions within Environment Sensitive Hydrogels, 2009, pp. 1090-1099, vol. 10, Biomacromolecules, American Chemical Society.
Kell Mortensen et al., Structural Study on the Micelle Formation of Poly(ethylene oxide)-Poly(propylene oxide)-Poly(ethylene oxide) Triblock Copolymer in Aqueous Solution, 1993, pp. 805-812, vol. 26, Macromolecules, American Chemical Society.
Mariko Morishita et al., Pluronic F-127 gels incorporating highly purified unsaturated fatty acids for buccal delivery of insulin, 2001, pp. 289-293, International Journal of Pharmaceutics, Elsevier.

(Continued)

Primary Examiner — Tracy Vivlemore
Assistant Examiner — Monica A Shin
(74) Attorney, Agent, or Firm — Hauptman Ham, LLP

(57) ABSTRACT

Disclosed is a composition for forming an injectable hydrogel. The composition includes 1% by weight or less of a graphene-based material and 5% by weight or more of a triblock copolymer. The triblock copolymer may be a copolymer represented by Formula 1:

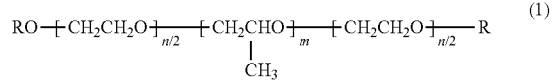

wherein n is an integer from 8 to 540, m is an integer from 16 to 70, and R is H or a vinylcarbonyl group ($CH_2$=CHCO—). When R in Formula 1 is a vinylcarbonyl group, the triblock copolymer may be cross-linked through the vinylcarbonyl group to form a nanogel. The composition can be prepared by a simple mixing process. In addition, the composition is substantially free from in vitro and in vivo stability problems encountered with conventional hydrogel compositions. Furthermore, the composition has high biocompatibility as well as excellent mechanical properties such as high storage modulus.

8 Claims, 18 Drawing Sheets

(56) References Cited

OTHER PUBLICATIONS

Ken-Hsuan Liao et al., Cytotoxicity of Graphene Oxide and Graphene in Human Erythrocytes and Skin Fibroblasts, 2011, pp. 2607-2615, vol. 3, ACS Publications, American Chemical Society.

Abhishek Sahu et al., Graphene oxide mediated delivery of methylene blue for combined photodynamic and photothermal therapy, 2013, pp. 6239-6248, Biomaterials, Elsevier.

Jianfeng Shen et al., Mechanical, thermal and swelling properties of poly(acrylic acid)-grapheneoxide composite hydrogels, 2012, pp. 1831-1836, vol. 8, Soft Matter, The Royal Society of Chemistry.

Zhiqiang Li et al., Preparation and characterization of pH- and temperature-responsive hydrogels with surface-functionalized graphene oxide as the crosslinker, pp. 3139-3145, vol. 8, Soft Matter, The Royal Society of Chemistry, Published 2012.

Lu Zhang et al., High strength graphene oxide/polyvinyl alcohol composite hydrogels, 2011, pp. 10399-10406, vol. 21, J. Mater. Chem., The Royal Society of Chemistry.

\* cited by examiner (A)

(B)

COMPOSITION FOR FORMING PLURONIC-BASED HYDROGEL WITH IMPROVED STABILITY

CROSS-REFERENCE TO RELATED APPLICATIONS

This application claims priority under 35 U.S.C. § 119 to Korean Patent Application No. 10-2014-0064945 filed on May 29, 2014 in the Korean Intellectual Property Office, the disclosure of which is incorporated herein by reference in its entirety. Further, this application also claims the priority of U.S. provisional patent application No. 61/942,234 filed on Feb. 20, 2014 in the United States Patent and Trademark Office.

BACKGROUND OF THE INVENTION

1. Field of the Invention

The present invention relates to a composition for forming an injectable hydrogel.

2. Description of the Related Art

Hydrogels are three-dimensional hydrophilic polymeric materials and possess numerous advantages such as biocompatibility, the ability to absorb water, and lowinflammatory responses. Hydrogels can also be used as reservoirs for sustained release of drugs or proteins. Particularly, injectable hydrogels are suitable for use in drug/protein delivery and tissue engineering. Injectable hydrogels can be prepared using responses to environmental stimuli such as temperature or pH. For example, such materials are flowable before administration, but once injected, they are rapidly converted into a gel state under physiological conditions. These systems enable mass delivery in a minimally invasive manner, are gelled at desired tissue sites, and minimize the formation of scars, resulting in a reduced risk of infection. Furthermore, bioactive molecules or cells can be incorporated into the gels by simple mixing prior to injection.

Polymers with lower critical solution temperature (LCST) characteristics are soluble below the LCST but become insoluble at or above the LCST, leading to gel formation. Accordingly, they can be utilized as thermosensitive injectable hydrogels. However, the application fields of such polymers are limited, mainly because of very rapid dissolution after injection. The reason for this limitation is that the injection sites of the body are not maintained in a sealed state but are excessively exposed to aqueous environments. There exist studies on the introduction of additional covalent crosslinking bonds, mainly by photopolymerization, in order to improve the stability of the gel state after injection (T. Vermonden, N. E. Fedorovich, D. vanGeemen, J. Alblas, C. F. van Nostrum, W. J. A. Dhert, W. E. Hennink, PhotopolymerizedThermosensitive Hydrogels: Synthesis, Degradation, and Cytocompatibility, Biomacromolecules, 2008, 919-926.; K. J. Jeong, A. Panitch, Interplay between covalent and physical interactions within environment sensitive hydrogels, Biomacromolecules, 2009, 10, 1090-1099).

Pluronics are triblock copolymers of hydrophobic propylene oxide and hydrophilic ethylene oxide and are widely applied as injectable hydrogel systems (K. Mortensen, J. S. Pedersen, Structural study on the Micelle Formation of Poly(ethylene oxide)-poly(propylene oxide)-poly(ethylene oxide) Triblock Copolymer in Aqueous solution. Macromolecules, 1993, 26, 805-812). Pluronics self-assembled into micelles in aqueous solution and exhibit temperature-responsive sol-gel transition behaviors at or above their critical micelle concentration (CMC) and critical micelle temperature (CMT) values. Gelation of Pluronic proceeds due to micellar packing at or above the CMT and a high concentration of Pluronic, bringing about a dramatic change in the rheological properties of the Pluronic. Based on this thermoreversible gelation, Pluronic F 127 (PF127) has been extensively investigated, especially as an injectable system for local delivery of drug (M. Morishita, J. M. Barichello, K. Takayama, Y. Chiba, S. Tokiwa, T. Nagai, Pluronic F127 gels Incorporating Highly Purified Unsaturated Fatty acids for Buccal delivery of Insulin, Int. J. Pharm., 2001, 212, 289-293). However, similarly to other physical gelation systems, PF127 hydrogels are very rapidly dissolved, which limits their applications. As a result, PF127 hydrogels suffer from very poor in vivo mechanical properties as well as very rapid drug release.

In recent years, biological applications of graphene have received great attention in various applications, for example, biosensors, nanocarriers for drug delivery, and probes for cellular and biological imaging. Graphene has a structure in which a monolayer of $sp^2$-hybridized carbon atom is arranged in a two-dimensional honeycomb crystal lattice. Graphene is considered as a planar aromatic macromolecule due to its π-conjugated layer structure. This planar structure gives a very high degree of surface area and imparts the ability to react with various materials, including metals, drugs, biomolecules and cells. However, graphene necessitates surfactants or surface modification for biological applications because it is highly hydrophobic and is not readily dispersible in water. In contrast, graphene oxide (GO) is an oxidized derivative of graphene and is a compound consisting of carbon, oxygen, and hydrogen in various ratios. GO has hydrophilic groups such as carboxyl, hydroxyl and epoxy groups, which impart water dispersibility. Although GO is relatively hydrophilic compared to graphene, the biocompatibility and toxicity of GO have not been elucidated to date. Most studies have reported that GO does not exhibit in vitro and in vivo toxicity, but some researchers have reported the toxicity of GO (K. H. Liao, Y. S. Lin, C. W. Macosko, C. L. Haynes, Cytotoxicity of graphene oxide and graphene in human erythrocytes and skin fibroblasts, ACS Appl. Mater. Interfaces, 2011, 3, 2607-2615). Under these circumstances, GO sheets modified with nontoxic polymers have been developed and investigated for bioapplications.

The present inventors also reported a stimulus-sensitive injectable hydrogel system composed of self-assembled graphene oxide nanosheets mediated by physical crosslinking of Pluronic in a low concentration solution of the Pluronic (Korean Patent Publication No. 10-2013-0115459). This hydrogel was reported to undergo a sol-gel transition in response to various stimuli and to form a stable gel without causing any noticeable immune reactions after in vivo subcutaneous injection. The present inventors also reported the fact that Pluronic-coated nano-graphene oxide functions as a delivery vehicle for photothermal materials and photosensitizers, creating synergistic effects in phototherapy (A. Sahu, W. I. Choi, J. H. Lee, G. Tae, Graphene oxide mediated delivery of methylene blue for combined photodynamic and photothermal therapy, Biomaterials, 2013, 34, 6239-6248). The two documents show a strong affinity between graphene oxide and Pluronic and reveal the fact that the GO-Pluronic composite systems have acceptable biocompatibility.

Several research groups have reported the fact that the introduction of GO considerably increased the mechanical and thermal properties of host polymers (J. Shen, B. Yan, T. Li, Y. Long, N. Li, M. Ye, Mechanical, thermal and swelling properties of poly(acrylic acid)-graphene oxide composite hydrogels, Soft Matter, 2012, 8, 1831-1836). Li et al. prepared pH- and temperature-responsive hydrogels using linear sodium alginate and GO-crosslinked poly(N-isopropylacrylamide)(PNIPAM) and reported that the GO composite hydrogel shave much stronger mechanical properties than GO-free hydrogels (Z. Li, J. Shen, H. Ma, X. Lu, M. Shi, N. Li, M. Ye, Preparation and characterization of pH- and temperature-responsive hydrogels with surface-functionalized graphene oxide as the crosslinker, Soft Matter, 2012, 8, 3139-3145). Zhang et al. reported the fact that GO as a nanofiller was introduced into polyvinyl alcohol (PVA) as a matrix to prepare composite hydrogels with improved tensile strength, elongation at break and compressive strength (L. Zhang, Z. Wang, C. Xu, Y. Li, J. Gao, W. Wang, Y. Liu, High strength graphene oxide/polyvinyl alcohol composite hydrogels, J. Mater. Chem., 2011, 21, 10399-10406). However, to the best of our knowledge, there has been no report on the use of GO for the purpose of improving the in vivo stability of physical gel systems.

SUMMARY OF THE INVENTION

The present invention is intended to provide a composition for forming a highly biocompatible, non-toxic, injectable hydrogel with good in vitro and in vivo stability.

One aspect of the present invention provides a composition for forming an injectable hydrogel including (A) 1% by weight or less of a graphene-based material and (B) 5% by weight or more of a triblock copolymer wherein (i) the triblock copolymer is a copolymer represented by Formula 1:

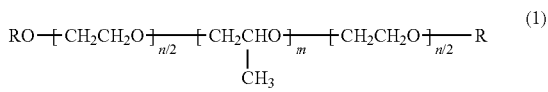

(1)

wherein n is an integer from 8 to 540, m is an integer from 16 to 70, and R is H or a vinylcarbonyl group ($CH_2=CHCO-$), or (ii) the triblock copolymer is the copolymer of Formula 1 wherein R is a vinylcarbonyl group and is crosslinked through the vinylcarbonyl group to form a nanogel.

According to one embodiment of the present invention, the graphene-based material may be selected from graphene oxide (GO), graphene oxide whose surface hydroxyl groups are substituted with carboxyl groups, reduced graphene oxide (rGO), and mixtures thereof.

According to a further embodiment of the present invention, in Formula 1, R may be H, n/2 may be 100, and m may be 65.

According to another embodiment of the present invention, in Formula 1, R may be a vinylcarbonyl group, n/2 may be 100, and m may be 65.

According to another embodiment of the present invention, the graphene-based material and the triblock copolymer may be included in amounts of 0.1 to 1% by weight and 5 to 50% by weight, respectively.

According to another embodiment of the present invention, the hydrogel-forming composition may include at least one solvent selected from the group consisting of distilled water, buffers, and physiological saline.

Another aspect of the present invention provides a sustained-release drug carrier including (1) the composition for forming an injectable hydrogel according to any one of the exemplary embodiments and (2) a protein drug.

According to one embodiment of the present invention, the protein drug may be a growth factor.

The hydrogel-forming composition of the present invention can be prepared by a simple mixing process. In addition, the composition of the present invention is substantially free from in vitro and in vivo stability problems encountered with conventional hydrogel compositions. Furthermore, the composition of the present invention has high biocompatibility as well as excellent mechanical properties such as high storage modulus.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
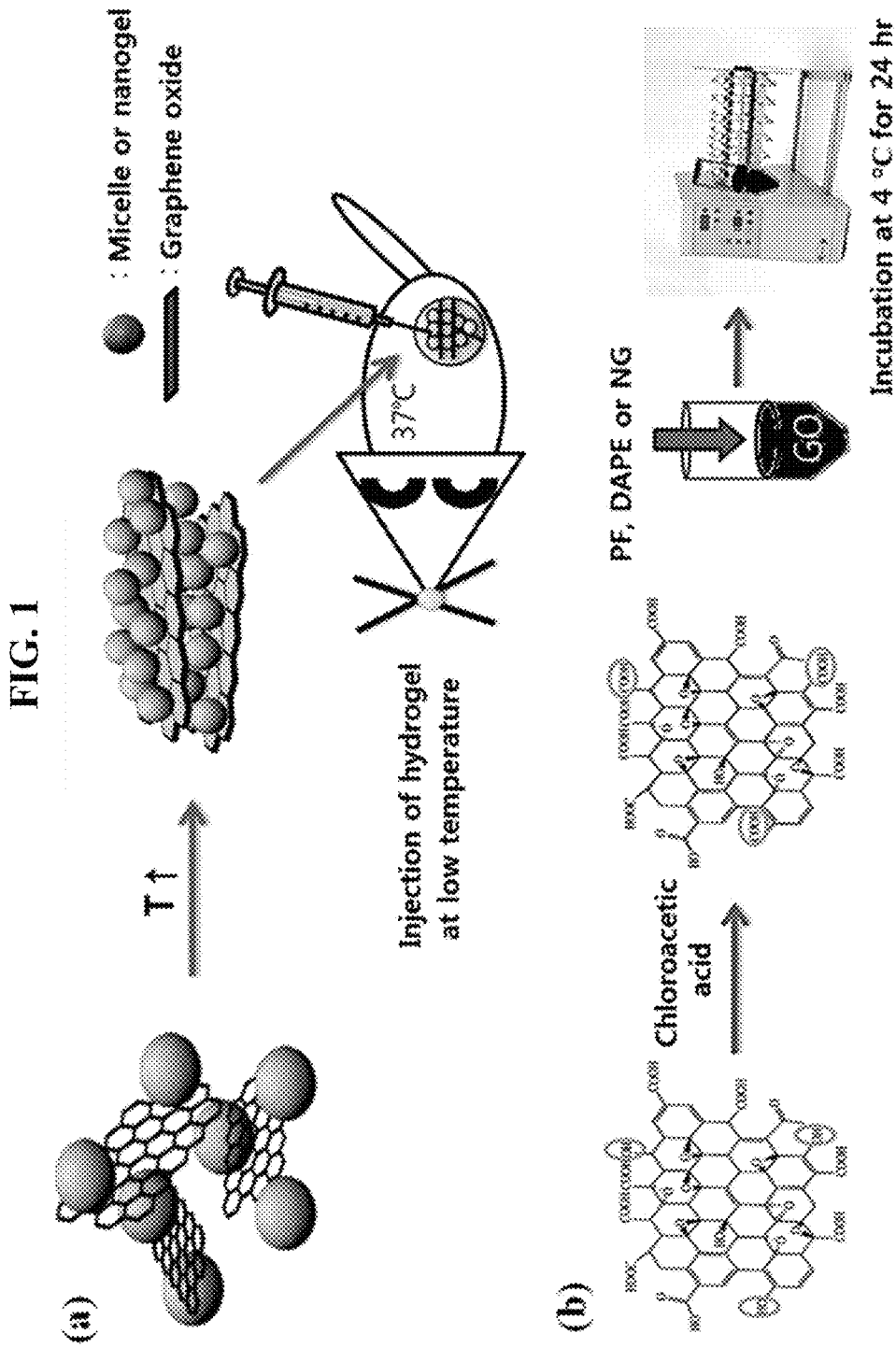
FIG. 1 shows schematic representations of (a) an injectable hydrogel system according to the present invention and (b) an exemplary process for preparing the hydrogel system.

The present invention provides a composition for forming an injectable hydrogel including (A) 1% by weight or less of a graphene-based material and (B) 5% by weight or more of a triblock copolymer wherein (i) the triblock copolymer is a copolymer represented by Formula 1:

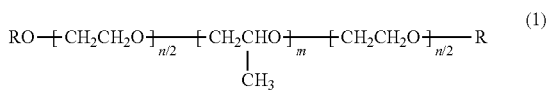

(1)

wherein n is an integer from 8 to 540, m is an integer from 16 to 70, and R is H or a vinylcarbonyl group ($CH_2$=CHCO—), or (ii) the triblock copolymer is the copolymer of Formula 1 wherein R is a vinylcarbonyl group and is crosslinked through the vinylcarbonyl group to form a nanogel.

The triblock copolymer of Formula 1 is a compound called poloxamer, which was developed by Irving Schmolka in 1973. The triblock copolymer of Formula 1 consists of a central hydrophobic polyoxypropylene block flanked by two hydrophilic polyoxyethylene blocks. This poloxamer is also widely known by the trade name "Pluronic (BASF)". Compositions for forming hydrogels based on Pluronics maintain sol states at low temperatures but form a hydrogel state by self-assembly when the temperature rises to around the body temperature. Accordingly, the composition of the present invention can be prepared by simply mixing the graphene-based material and the triblock copolymer at the defined concentrations with stirring at a low temperature. The composition of the present invention can be gelled by raising the temperature to around the body temperature. However, as described above, conventional Pluronic-based hydrogel systems are very rapidly dissolved after injection because the injection sites of the body are not maintained in a sealed state but are exposed to aqueous environments. Due to this instability, the conventional hydrogel systems suffer from the problems of rapid drug release and poor mechanical properties.

Thus, the present inventors have discovered that Pluronic-based hydrogel systems including a small amount of the graphene-based material have markedly improved in vitro and in vivo stability compared to existing hydrogel systems. The present invention has been accomplished based on this discovery.

In the present invention, the triblock copolymer and the graphene-based material are present in amounts of 5% by weight or more and 1% by weight or less, respectively, based on the total weight of the composition. Particularly preferably, the graphene-based material and the triblock copolymer are included in amounts of 0.1 to 1% by weight and 5 to 50% by weight, respectively.

Within these ranges, the composition of the present invention can effectively form a hydrogel with improved stability. If the content of the triblock copolymer is less than 5% by weight or exceeds 50% by weight or the content of the graphene-based material exceeds 1% by weight or is less than 0.1% by weight, a hydrogel with desired physical properties cannot be formed. Therefore, it is very important to adjust the contents of the graphene-based material and the triblock copolymer to the ranges defined above.

The graphene-based material may be selected from graphene oxide (GO), graphene oxide whose surface hydroxyl groups are substituted with carboxyl groups, reduced graphene oxide (rGO), and mixtures thereof. The addition of GO-COOH instead of GO enables the preparation of hydrogels with improved storage moduli, which can be seen from the Examples Section that follows. This is because the carboxyl groups of GO-COOH leads to an increase in the number of hydrogen bonds to further promote the interaction between the triblock copolymer (e.g., Pluronic) and the graphene-based material and therefore GO-COOH can improve the stability of Pluronic-based hydrogels compared to GO.

Various triblock copolymers may be used in the present invention, and examples thereof include, but are not limited to, copolymers sold under the trade name Pluronics (BASF), such as PluronicF127 and PluronicP105. For example, Pluronic F127 is the compound represented by Formula 2:

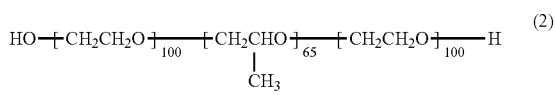

(2)

The triblock copolymer may be the diacrylatedtriblock copolymer represented by Formula 3:

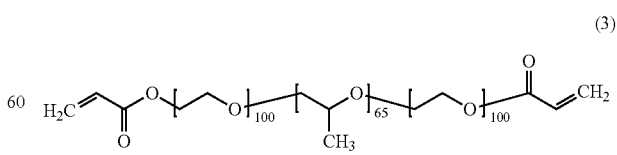

(3)

The diacrylatedPluronic (DAPF) is more hydrophobic than Pluronic (PF), thus being effective in increasing the storage modulus of hydrogels and further improving the in vitro and in vivo stability of hydrogels.

The diacrylatedtriblock copolymer represented by Formula 3 may form a nanogelphase. In this connection, the present inventors have reported the preparation of a nanogelphase triblock copolymer by simple photo-crosslinking (W. I. Choi, G. Tae, Y. H. Kim, One pot, single phase synthesis of thermo-sensitive nano-carriers by photo-crosslinking of a diacrylatedpluronic, J. Mater. Chem., 2008, 18, 2769-2774), the disclosure of which is incorporated herein by reference in its entirety.

Particularly, the nanogel phase triblock copolymer (NG) undergoes gelation at a lower concentration and a lower temperature than PF or DAPF. NG is not changed to a sol state even at high temperature. The reason is believed to be because the nanogels are chemically crosslinked.

The present invention also provides a sustained-release drug carrier including (1) the composition for forming an injectable hydrogel and (2) a protein drug.

According to one embodiment of the present invention, the protein drug may be a growth factor.

In addition, NG exhibits high stability under both in vitro and in vivo environments. Due to these advantages, NG can function as a good sustained-release drug carrier.

Any solvent capable of dissolving the graphene-based material and the triblock copolymer may be used without limitation in the present invention. Examples of such solvents include various aqueous solutions, such as distilled water, buffers, and physiological saline. These solvents may be used alone or as a mixture of two or more thereof.

The hydrogel-forming composition of the present invention can be prepared through simple mixing and subsequent incubation. FIG. 1(b) schematically shows a method for preparing the hydrogel-forming composition of the present invention. The composition of the present invention can easily undergo a phase transition from a sol state to a gel state in response to various external stimuli. Examples of such stimuli include temperature rise, pH reduction, and near-infrared irradiation. A detailed description of the external stimuli can also be found in Korean Patent Publication No. 10-2013-0115459 which was filed by the present applicant, the disclosure of which is incorporated herein by reference in its entirety.

The present invention will be explained in more detail with reference to the following examples. However, these examples are provided to assist in understanding the invention and are not intended to limit the scope of the present invention.

Experimental Materials

Pluronic F127 (PEO100 PPO65 PEO100, MW 12.6 kDa) was donated from BASF (Seoul, Korea). Acryloyl chloride, triethylamine, anhydrous toluene, monobasic potassium phosphate, dibasic sodium phosphate, potassium chloride, sodium chloride, and sodium azide were purchased from Sigma-Aldrich (St. Louis, Mo., USA). Anhydrous diethyl ether was purchased from Fisher Scientific Inc. (Pittsburgh, Pa., USA). 4-(2-Hydroxyethoxy)phenyl-(2-hydroxy-2-propyl)ketone (Irgacure 2959) was purchased from Ciba Specialty Chemicals Inc. (Basel, Switzerland). Single layer graphene oxide (X, Y dimension <500 nm) in the form of a 0.5% (w/v) solution was purchased from Angstrom Materials Inc. (OH, USA). Chloroacetic acid and sodium hydroxide were purchased from Aldrich (WI, USA). Dialysis membranes [MWCO 50,000 & 3,500] manufactured by Spectrum Laboratories, Inc. (Houston, Tex., USA) were used. 0.2 μm cellulose sterile syringe filters and 0.8 μm cellulose sterile syringe filters were purchased from Toyo Roshi Kaisha. Ltd. (Tokyo, Japan). 0.2 μm nylon syringe filters were purchased from Whatman (Florham Park, N.J., USA). Human vascular endothelial growth factor (hVEGF) and ELISA development kits were purchased from Pepro-tech (Rocky Hill, N.J., USA).

Synthesis of diacrylatedPluronic

DiacrylatedPluronic F127 (DA-PF 127) was synthesized as reported in the literature (W. I. Choi, G. Tae, Y. H. Kim, One pot, single phase synthesis of thermo-sensitive nano-carriers by photo-crosslinking of a diacrylatedpluronic, J. Mater. Chem., 2008, 18, 2769-2774). Specifically, 5 g of dry Pluronic F127 was allowed to react with 10 moles of excess triethylamine and acryloyl chloride with stirring in 100 mL of an hydroustoluene under an argon atmosphere for at least 17 hr. The obtained product was precipitated with anhydrous diethyl ether in an ice-water bath, filtered, and dried under vacuum for a few days. The numbers of the acryl protons (=$CH_2$, 5.7-6.4 ppm) and methyl protons (—$CH_3$, 1.1 ppm) in the propylene oxide units were confirmed by 400 MHz $^1$H-NMR spectroscopy ($D_2O$, JNM-ECX-400P, JEOL, Japan). As a result, the degree of acrylation of the diacrylatedPluronic was determined to be 98% or more.

Preparation of Nanogel Phase Pluronic

Nanogel phase Pluronic was prepared by simple photo-crosslinking, as reported by the present inventors (W. I. Choi, G. Tae, Y. H. Kim, One pot, single phase synthesis of thermo-sensitive nano-carriers by photo-crosslinking of a diacrylatedpluronic, J. Mater. Chem., 2008, 18, 2769-2774). Specifically, 10 wt % of diacrylatedPluronic (DA-PF127) was dissolved in DIW and filtered through a 0.2 μm cellulose acetate sterile syringe filter. The filtrate was diluted with DIW to prepare a solution containing 0.77 wt % of the diacrylatedPluronic. Irgacure 2959 as a photoinitiator was dissolved in 70% (v/v) ethanol and DIW, filtered through a 0.2 μm nylon filter, and added to the dilute DA-PF127 solution until the photoinitiator concentration reached 0.05 wt %. Next, the resulting solution was irradiated with UV from an unfiltered UV lamp (VL-4.LC, 8W, VilberLourmat, France) at an intensity of 1.3 mWcm$^{-2}$ for 15 min. Finally, unreacted precursors were removed by dialysis using a dialysis bag (MWCO 50,000) for 1 day.

Preparation of Carboxylated Graphene Oxide (GO-COOH)

A suspension of carboxylated GO sheets was prepared by chemical treatment and sonication in accordance with the method reported by Zhang et al. (W. Zhang, Z. Guo, D. Huang, Z. Liu, X. Guo, H. Zhong, Synergistic effect of chemo-photothermal therapy using PEGlyated graphene oxide, Biomaterials, 2011, 32, 8555-8561). Specifically, a 0.1 w/v % dispersion of GO (0.5 w/v %) in DIW was prepared, and then chloroacetic acid (150 mg) and sodium hydroxide (200 mg) were added thereto. The solution was stirred at 45° C. overnight. Subsequently, the resulting solution was sonicated using a 750 W, 30% intensity ultrasonic probe (Vibra-cell VCX 500, Sonics & Materials Inc., Newtown, Conn., USA) for 2 hr and was dialyzed against deionized water (dialysis bag MWCO 3,500) for a few days until neutrality. After dialysis, the suspension was subjected to sonication for 30 min and filtered through a 0.8 μm cellulose acetate filter. The size of the carboxylated GO was analyzed using an electrophoretic light scattering spectrometer (632.8 nm, ELS-8000, Otsuka Electronics Co., Japan).

Preparation of Injectable Sol-State Hydrogels

Each of PF 127, DA-PF, and NG was stirred and dissolved in the GO-COOH solution using a rotating stirrer at 4° C. for 48 hr to prepare three different kinds of hydrogels. The final concentrations of PF 127 and DA-PF were 17 wt %, and that of NG was 11 wt %. GO-COOH was used at three different concentrations: 0.04, 0.08, and 0.1 wt %.

Measurement of Rheological Properties

The rheological properties of the hydrogels were measured using a rheometer with a 15 mm diameter parallel plate geometry and roughened surface (Gemini, Malvern Instruments, Malvern, Worcestershire, UK). The gap between the plates was set to 0.45 nm and the volume of each sample was 100 µl. The temperature of the plates was lowered to 4° C., and subsequently the gelation kinetics of the samples was measured at 37° C. For the measurement of gelation kinetics, a single frequency of 1 rad/s was used at different GO concentrations for 36 min. Then, a frequency sweep of 0.1 to 100 rad/s was performed at a constant shear strain of 0.1% at 37° C.

Sol-gel Transition Phase Diagrams

The sol-gel transition phase diagrams of the hydrogels containing GO-COOH were constructed by the vial tilting method. Each sample in PBS solution was prepared in a 1.5 mL tube and put into a water bath. The temperature was gradually increased from 4° C. by 3° C. The gelpoint temperature of the sample was defined as the temperature at which no flowability of the sample was observed for 1 min after the test tube was inverted. The GO concentration was set to 0.1 wt % (n=3).

In vitro Degradation Rates of the Hydrogels

The degradation rates of the hydrogels were measured to analyze the stability of the hydrogels. Each of Pluronic (PF), the PF-GO hydrogel, the PF-GO-COOH hydrogel, DA-PF, the DAPF-GO-COOH hydrogel, nanogelphase PF (NG), and the NG-GO-COOH hydrogel was placed at the bottom of a 15 ml tube. The volume of each hydrogel was 200 µl. After gelation, 5 ml of a release buffer (PBS containing 2 mM % sodium azide) was put into the 15 ml tube. The samples were stored in a shaking incubator at 37° C. and 1000 rpm (SI-600R, Lab. Companion, JEIO TECH, city, Korea). The whole release buffer was replaced with a fresh one each time and the residual volumes of the hydrogels were measured (n=3).

In vitro VEGF Release Experiment

VEGF solutions were prepared and the rates of VEGF released from the hydrogels were measured. Specifically, the hydrogels loaded with VEGF were prepared by the following procedure. First, each of lyophilized Pluronic, diacrylatedPluronic, and nanogel phase Pluronic was added to a VEGF solution and incubated using a rotating stirrer at 4° C. for 24 hr. Subsequently, graphene oxide (GO) was added and incubated under stirring at 4° C. for 24 hr. The final concentrations of the Pluronic and the diacrylatedPluronic were 17 wt %, that of the nanogelphase Pluronic was 11 wt %, and that of the added GO was 0.1 wt %. Each of the VEGF-loaded hydrogels was prepared at the bottom of a 15 ml tube. 5 ml of PBS containing 2 mM sodium azide and BSA were added and placed in a shaking incubator at 37° C. and 100 rpm. The whole release medium was replaced with a fresh one each time. The amounts of VEGF released were measured using ELISA development kits.

In vivo Animal Experiment

Male BALB/c mice (aged 8 weeks) were used to investigate the in vivo stability and biocompatibility of the hydrogels. All animals were purchased from Orient Bio Inc. (Seoul, Korea) and were handled in accordance with the guidelines of the Animal Care and Use Committee of Gwangju Institute of Science and Technology (GIST). Each hydrogel in the sol state at 4° C. was subcutaneously injected into the back of mice through a syringe with a 22 G needle. In order to investigate the in vivo stability of the hydrogels after injection, the sizes of the hydrogels were monitored at predetermined time points: 1 day, 1 week, 2 weeks, 4 weeks, and 8 weeks post-injection.

For biocompatibility analysis, immunohistological staining was performed. After the animals were sacrificed, the skin sites including the gels were excised. The skin sites were fixed in 10% formalin, dehydrated in alcohol, and embedded in paraffin. The paraffin was sectioned to a thickness of 5µ musing a slicer and stained with hematoxylin and eosin (H&E). The stained sections were observed using an optical microscope.

Experimental Results

1. Effects of GO on Mechanical Properties of Hydrogels

Figure 3:
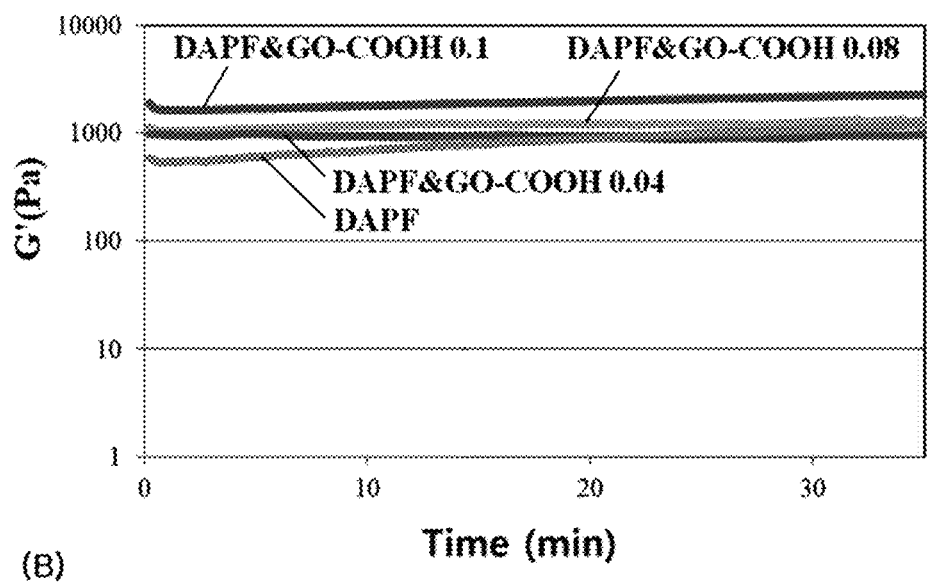
FIG. 3 graphically shows the gelation kinetics of hydrogels composed of 17% by weight of DAPF and GO-COOH at 37° C.: (A) single frequency curves at different GO concentrations and (B) a frequency sweep curve of a DAPF/GO-COOH hydrogel composed of 17% by weight of DAPF and 0.1% by weight of GO-COOH.
Figure 3:
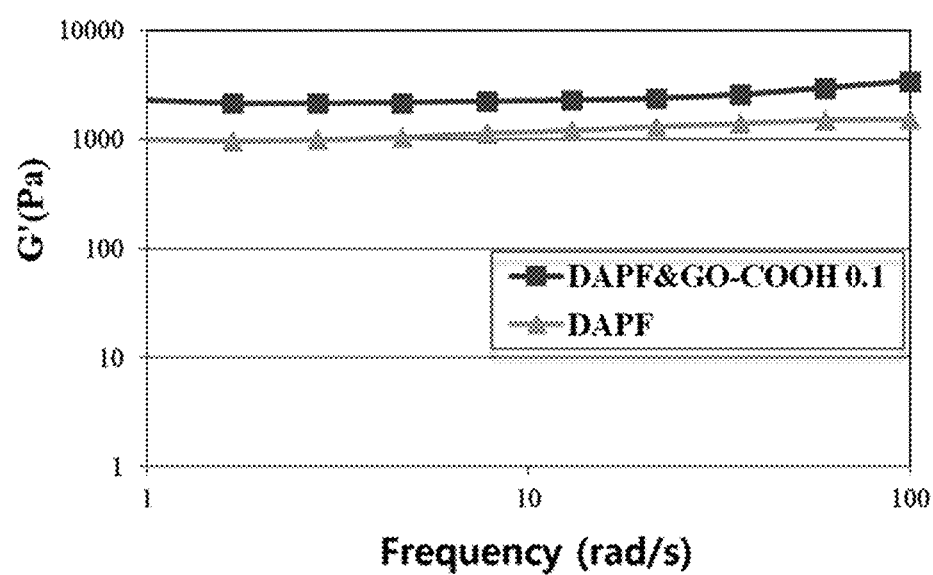

Hydrogels containing 17 wt % of Pluronic (PF), 17 wt % of diacrylatedPluronic (DAPF), and 11 wt % nanogel phase Pluronic(NG) in PBS were prepared. The gelation kinetics and storage moduli of the hydrogels were measured using a rheometer. The hydrogels in the sol state were loaded on a parallel plate geometric holder at 4° C. Subsequently, in situ gelation was achieved at an elevated temperature of 37° C. The Pluronic molecules exist in the form of micelles at or above the CMT and CMC and can form a physical gel state at a high concentration through micellar packing. The gelation process of DAPF should be similar to that of PF. However, the storage modulus of DAPF is slightly higher than that of PF, presumably because DAPF is more hydrophobic than PF (FIG. 3). The storage modulus of NG (FIG. 4) was similar to those of the DAPF hydrogels at a lower concentration (11 wt %) than PF or DAPF (17 wt %). The size of the chemically crosslinked basic structural unit of NG was ~60 nm at 37° C., which is larger than the micelle size of PF(~20 nm). NG underwent a sol-gel transition at a much lower temperature than PF micelles, which will be described in more detail.

Figure 2:
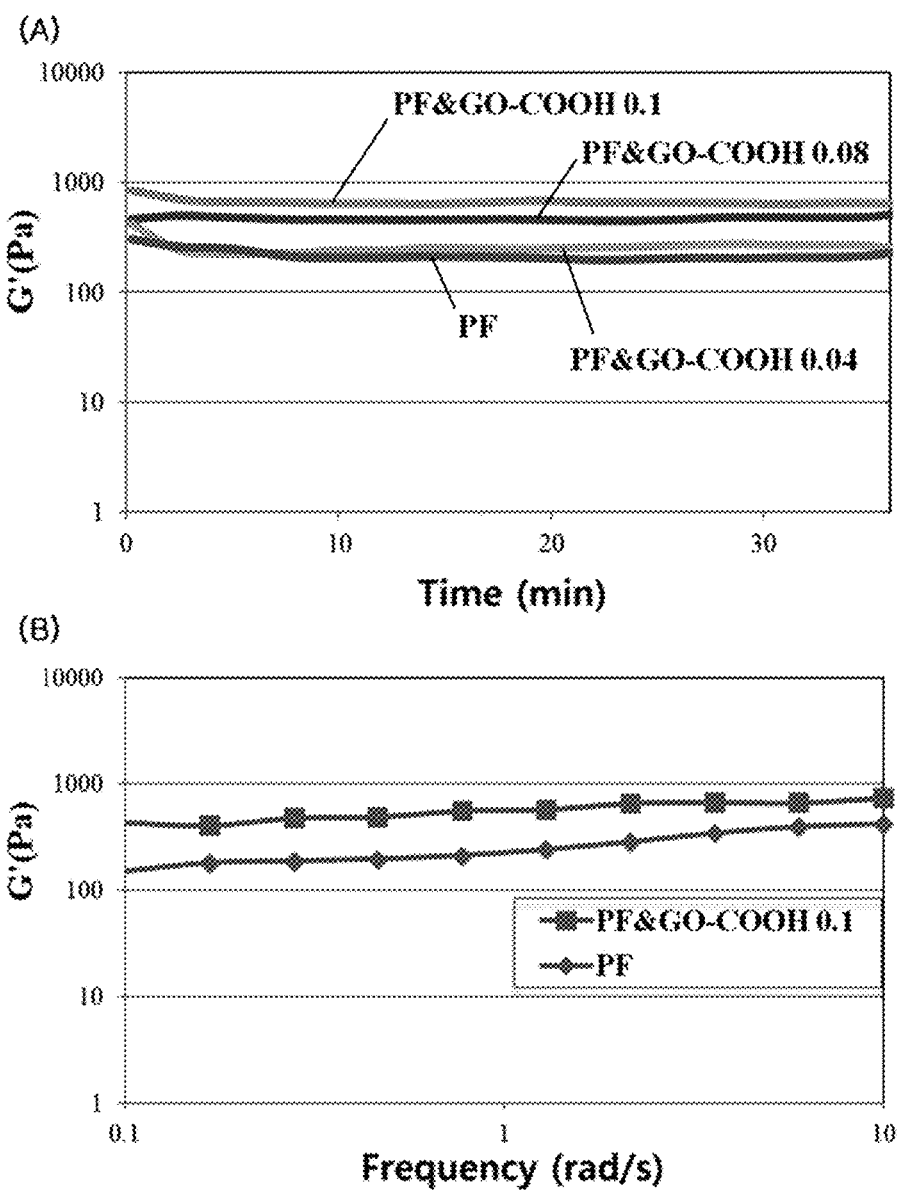
FIG. 2 graphically shows the gelation kinetics of hydrogels composed of 17% by weight of PF and GO-COOH at 37° C.: (A) single frequency curves at different GO concentrations and (B) a frequency sweep curve of a PF/GO-COOH hydrogel composed of 17% by weight of PF and 0.1% by weight of GO-COOH.
Figure 4:
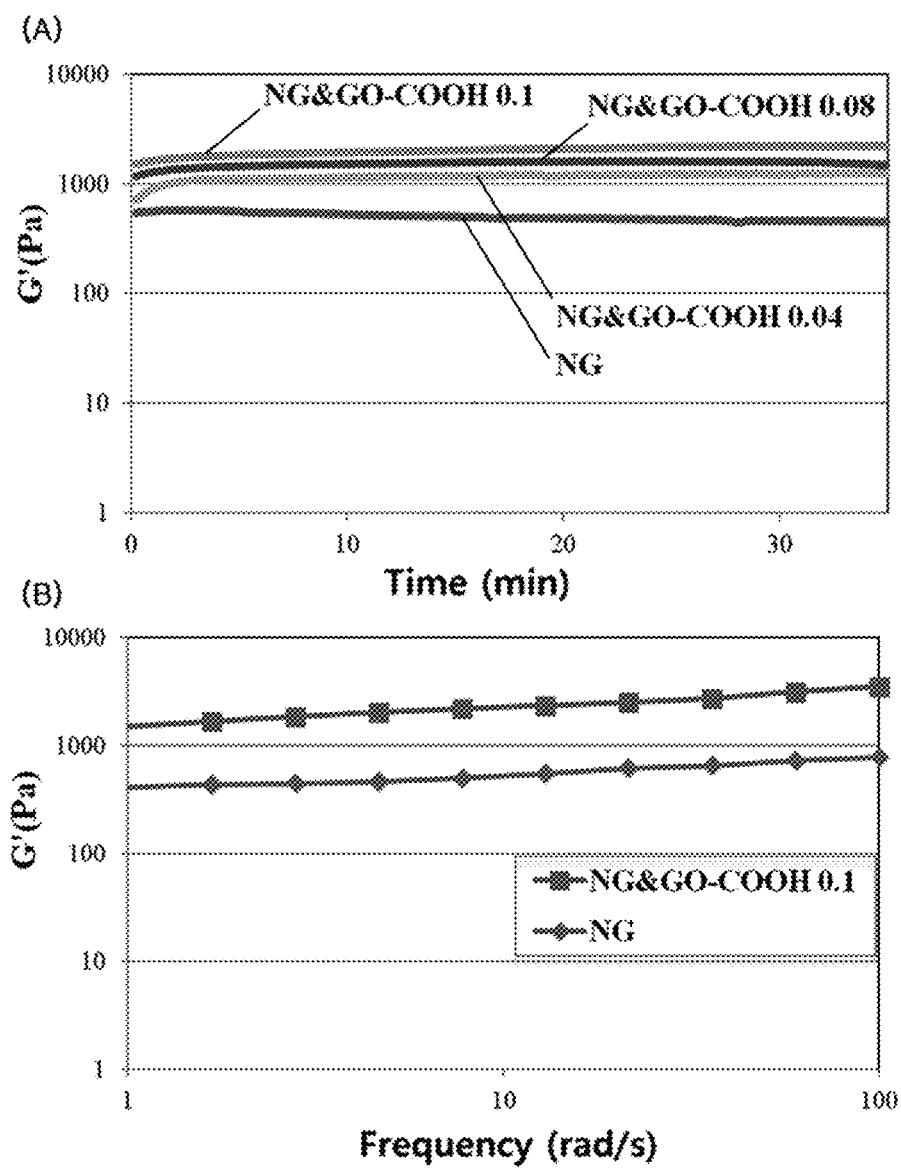
FIG. 4 graphically shows the gelation kinetics of hydrogels composed of 11% by weight of NG and GO-COOH at 37° C.: (A) single frequency curves at different GO concentrations and (B) a frequency sweep curve of a NG/GO-COOH hydrogel composed of 11% by weight of NG and 0.1% by weight of GO-COOH.
Figure 8:
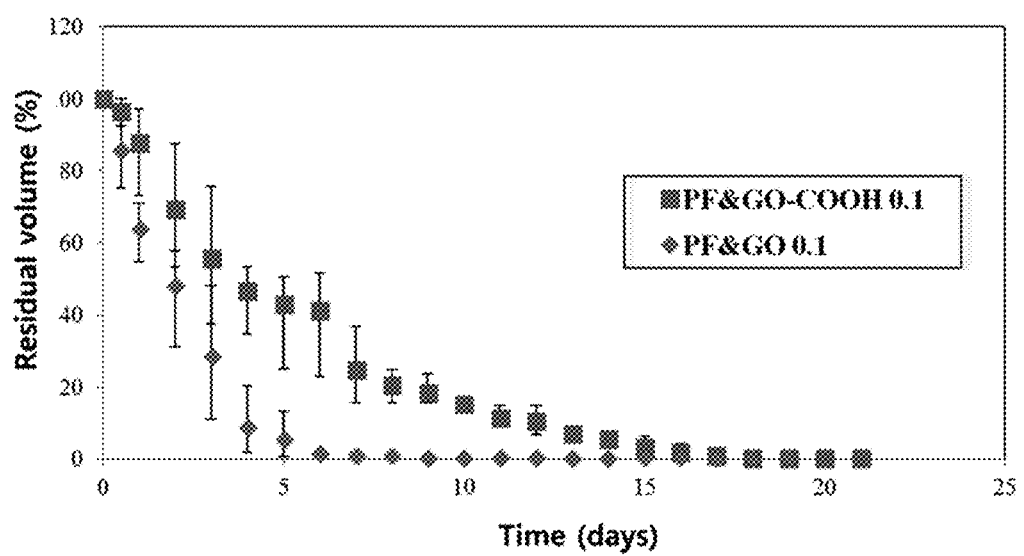
FIG. 8 is a graph showing changes in the degradation rate of hydrogels(n=3) composed of 17% by weight of PF and carboxylated GO and hydrogels including 17% by weight of PF and GO in PBS containing 2 mM sodium azidein a shaking incubator at 37° C. and 100 rpm.

The storage moduli of all hydrogels were improved by the addition of GO-COOH. In addition, the storage moduli of the hydrogels increased with increasing GO-COOH concentration from 0.04 wt % to 0.1 wt % at the same polymer concentration (FIGS. 2, 3, and 4). Therefore, the addition of GO-COOH was effective in improving the mechanical properties of all hydrogels. This appears to be probably due to the formation of effective physical crosslinking bonds by the addition of GO-COOH. As described previously, GO nanosheets strongly interact with Pluronic, which is achieved by hydrophobic interaction and hydrogen bonding. The level of contribution of the hydrophobic interaction can be supported by the fact that relatively more hydrophobic Pluronic P105 or F127 strongly interacts with GO while relatively less Pluronic PF68 does not strongly interact with GO. The level of contribution of the hydrogen bonding can be confirmed from the fact that this interaction is dependent on pH and the degree of oxygenation of GO. Accordingly, the carboxyl groups of GO-COOH leads to an increase in the number of hydrogen bonds to further promote the interaction between Pluronic and graphene. Indeed, as shown in FIG. 8, GO-COOH can more significantly increase the stability of the PF hydrogels than GO. Therefore, GO-COOH was used instead of GO in all other experiments.

The formation of stable gels can also be confirmed from the fact that the various hydrogels exhibit storage moduli substantially independent of frequency. At all frequencies, the storage moduli of the composite hydrogels were higher than those of the Pluronic-based hydrogels containing no GO-COOH.

Sol-gel Transition Phase Diagrams

PF, DAPF and NG undergo thermoreversiblesol-gel phase transition phenomena due to micelle or nanogel packing.

Figure 5:
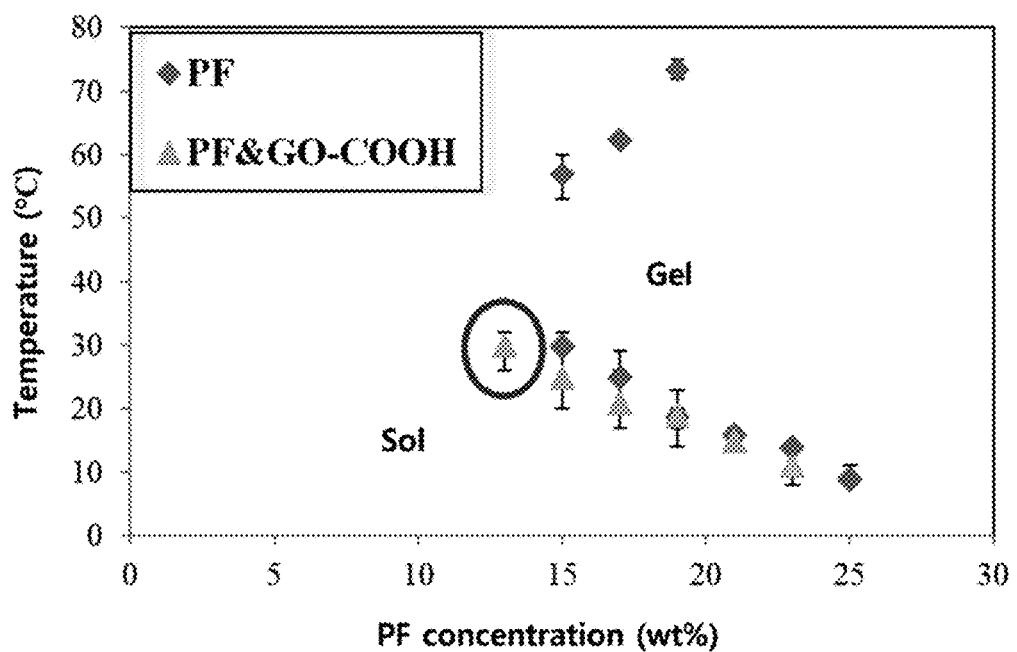
FIG. 5 shows sol-gel transition curves of PF and PF/GO-COOH hydrogels (GO 0.1% by weight, n=3) in PBS.
Figure 6:
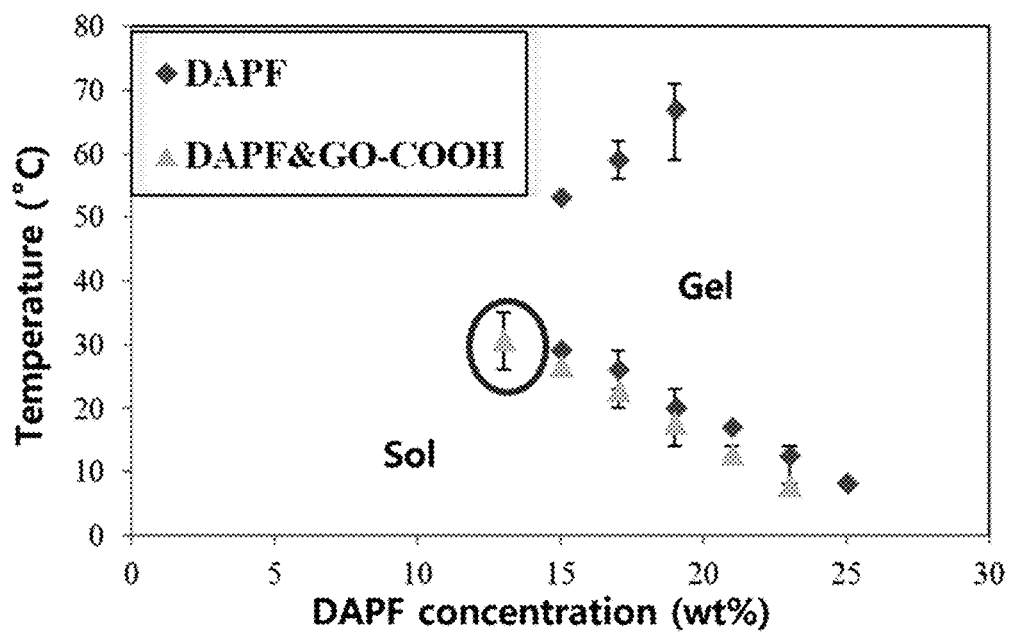
FIG. 6 shows sol-gel transition curves of DAPF and DAPF/GO-COOH hydrogels (GO 0.1% by weight, n=3) in PBS.

The influence of GO-COOH addition on the phase boundaries of the sol-gel transitions was analyzed. The sol states of the hydrogels were prepared in PBS buffer containing 0.1 wt % of GO-COOH. The sol-gel transitions were monitored by the vial tilting method with increasing temperature by 3° C. For PF and DAPF, the phase boundaries showing sol-to-gel transitions were not significantly changed despite the addition of GO-COOH at the fixed Pluronic concentrations with increasing temperature. In contrast, the phase boundaries showing gel-to-sol transitions disappeared at higher temperatures (FIGS. 5 and 6). The effects of GO-COOH were observed in the rheometer results, but the lower phase boundaries of the PF and DAPF hydrogels containing GO-COOH did not show significant differences. However, the gels were formed at the lower concentrations (13 wt %) when GO-COOH was added but the gels containing no GO-COOH were not formed at the same concentrations. The largest difference was that no upper phase boundaries were observed in the hydrogels containing GO-COOH. Gel-to-sol transitions are caused when the PEO chains are shortened and the micellar packing is thus loosened with increasing temperature. GO-COOH can strongly interact with the micelle molecules in the hydrogel networks to prevent loosening of the micellar packing. The micellar packing is maintained at high temperatures and the hydrogels do not become sol states.

Figure 7:
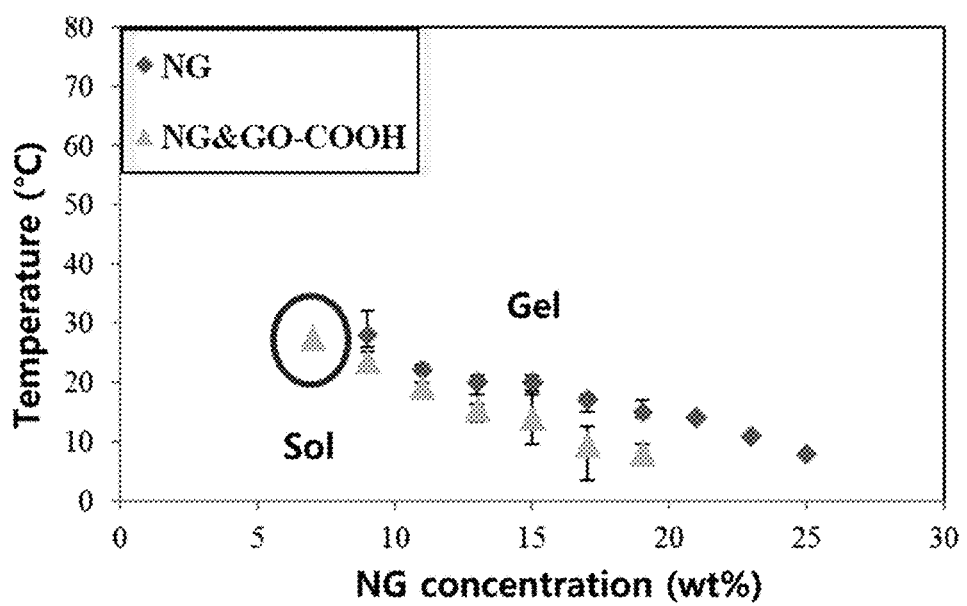
FIG. 7 sol-gel transition curves of NG and NG/GO-COOH hydrogels (GO 0.1% by weight, n=3) in PBS.

However, the nanogel phase Pluronic underwent gelation at a lower concentration and a lower temperature than PF or DAPF. Moreover, the NG hydrogels were not changed to a sol state even at high temperatures, because the nanogels were chemically crosslinked. The nanogels interact with each other and thus packing is not loosened. At the fixed concentrations, the NG/GO-COOH gels had lower phase boundaries than the gels containing no GO-COOH. The sol states of the NG/GO-COOH gels were changed to gel states at lower concentrations (FIG. 7). These experimental results show that the interaction between GO-COOH and the nanogels accelerated gelation. GO-COOH participated in the stabilization of the micellar packing, thus increasing the interaction of the networks. This structural stabilization is believed to reduce the critical gelation concentration and temperature.

In vitro Degradation Rates of the Hydrogels

To investigate the effects of GO-COOH addition on the stability of the Pluronic-based hydrogels, the in vitro degradation rates of the hydrogels were analyzed under stirring conditions at 37° C. The volume of each hydrogel remaining in the excess buffer was checked and the buffer was replaced with a fresh one daily. As expected, all physical gels without GO were rapidly degraded in the excess aqueous environment; the PF and DAPF gels were degraded within one day, and the NG gels were degraded within 7 days. Since the nanogels were chemically crosslinked, the aggregated NG gels showed lower degradation rates than the PF or DAPF gels.

The stability of all hydrogels was markedly improved by the addition of GO-COOH. First, the degradation rates of the hydrogels composed of 17 wt % of PF and 0.1 wt % of GO and the hydrogels composed of 17 wt % of PF and 0.1 wt % of GO-COOH were compared to analyze the difference between carboxylated GO (GO-COOH) and unmodified GO (FIG. 8). GO-COOH was prepared by reacting GO with chloroacetic acid ($ClCH_2COOH$) under basic conditions. As a result of the reaction, the hydroxyl groups (—OH) of GO were substituted with carboxyl groups (—COOH). The difference between GO-COOH and GO was found to be significant when improved stability of the PF hydrogels was taken into consideration; almost all PF/GO hydrogels were degraded within 5 days, while 40% or above of the PF/GO-COOH hydrogels remained undegraded for the same time period. This large difference is attributed to the increased number of hydrogen bonds provided by GO-COOH and the fact that better dispersibility of GO-COOH in the physiological buffer by the increased negative charges. Therefore, GO-COOH is more uniformly distributed in the hydrogels than GO. For these reasons, GO-COOH was used instead of GO in all other experiments.

Figure 9:
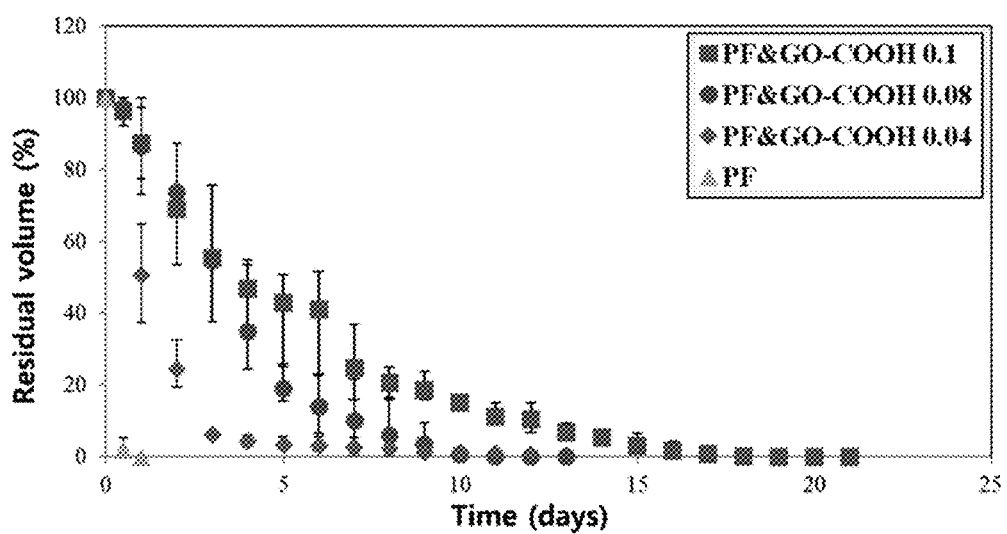
FIG. 9 is a graph showing changes in the degradation rate of hydrogels(n=3) composed of 17% by weight of PF and carboxylated GO in PBS containing 2 mM sodium azidein a shaking incubator at 37° C. and 100 rpm, as a function of GO content.
Figure 10:
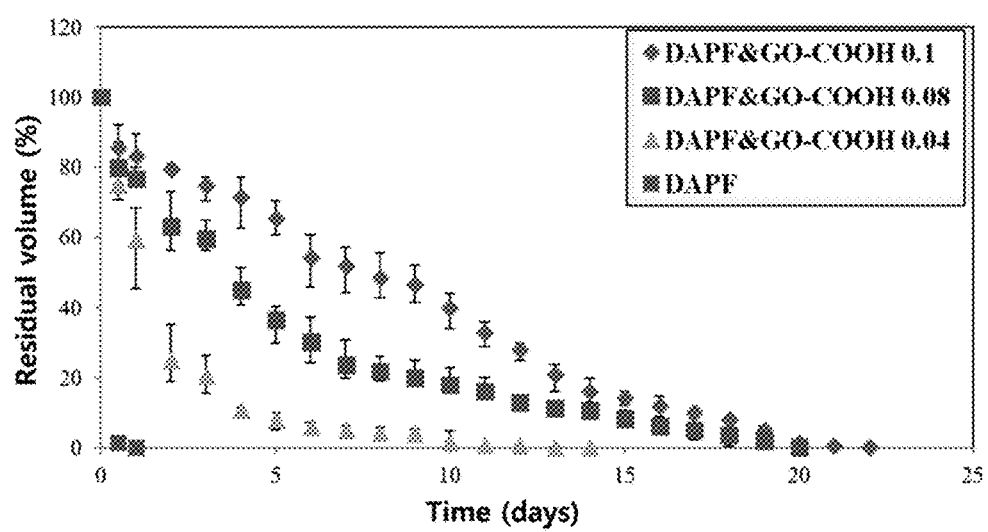
FIG. 10 is a graph showing changes in the degradation rate of hydrogels(n=3) composed of 17% by weight of DAPF and carboxylated GO in PBS containing 2 mM sodium azidein a shaking incubator at 37° C. and 100 rpm, as a function of GO content.
Figure 11:
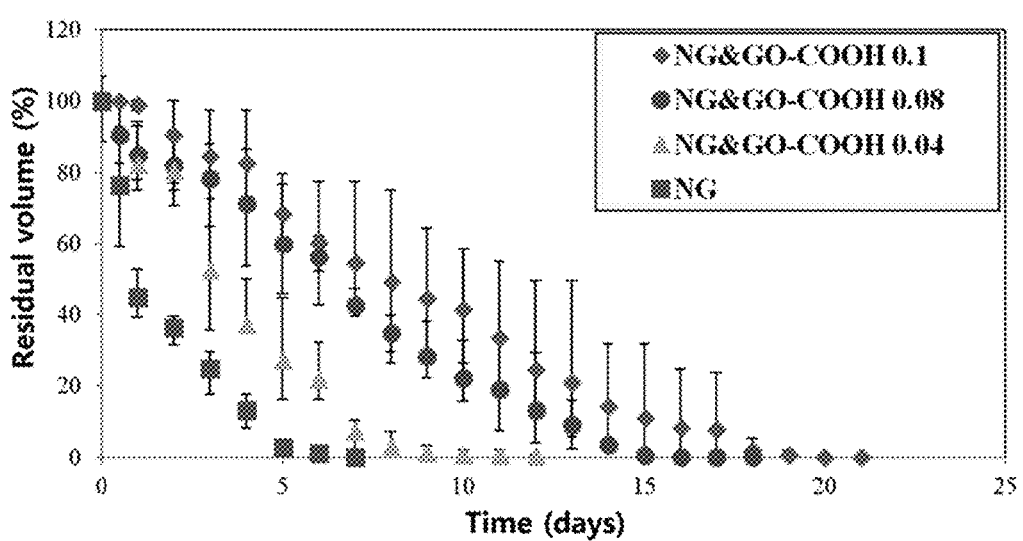
FIG. 11 is a graph showing changes in the degradation rate of hydrogels(n=3) composed of 11% by weight of NG and carboxylated GO in PBS containing 2 mM sodium azidein a shaking incubator at 37° C. and 100 rpm, as a function of GO content.

The stability of the hydrogels containing GO-COOH was evaluated at increasing concentrations of GO-COOH. The degradation rates of the PF hydrogels were observed to be considerably low even when the GO-COOH concentration was 0.04 wt %. The degradation rates were further reduced when the GO-COOH concentration was increased to 0.08 wt %. The degradation rates of the PF hydrogels containing 0.08 wt % of GO-COOH were comparable to those of the PF hydrogels containing 0.1 wt % of GO-COOH for the first 3 days, but distinct differences in degradation rate were observed after the fourth day (FIG. 9). At least 15 days were taken for complete degradation of the PF gels containing 0.1 wt % of GO-COOH while the PF gels were completely degraded within one day. Similarly, the degradation rates of the DAPF gels and the NG gels were greatly decreased in a concentration dependent manner by the addition of GO-COOH (FIGS. 10 and 11). The DAPF gels with slightly higher storage moduli were degraded slightly more slowly than the PF gels (FIGS. 2 and 3). Overall, the degradation rates of the Pluronic-based hydrogels can be systematically controlled by the GO-COOH content leading to an increase in storage modulus (FIGS. 2, 3, and 4).

The addition of GO-COOH led to an improvement in the mechanical properties of the Pluronic-based hydrogels and caused sol-to-gel transitions at lower concentrations. Gel-to-sol transitions were not observed even when the temperature was increased at fixed concentrations. However, such changes were not noticeable. In contrast to this, the addition of a small amount of GO-COOH achieved markedly improved stability of the physical hydrogels in open environments, suggesting the possibility that the injectable hydrogel system of the present invention can stay at the site of injection in an open environment, such as in vivo, for a time sufficient for practical applications.

In vitro VEGF Release from the Hydrogels

Figure 12:
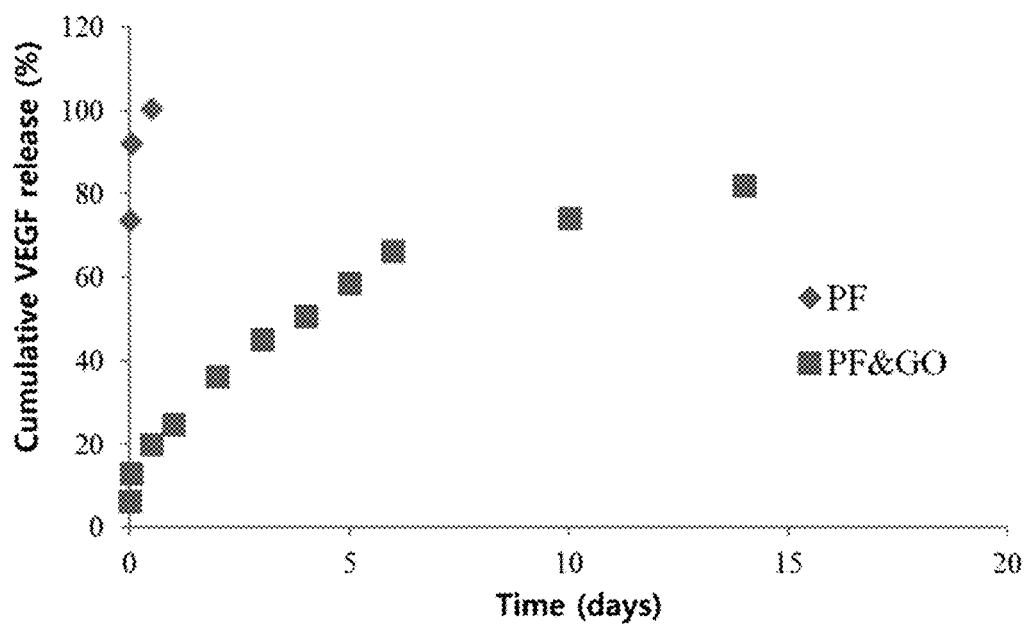
FIG. 12 shows VEGF release profiles of a hydrogel (♦) composed of 17% by weight of PF and a hydrogel (■) composed of PF and 0.1% by weight of carboxylated GO-COOH in PBS containing 2 mM sodium azidein a shaking incubator at 37° C. and 100 rpm.
Figure 13:
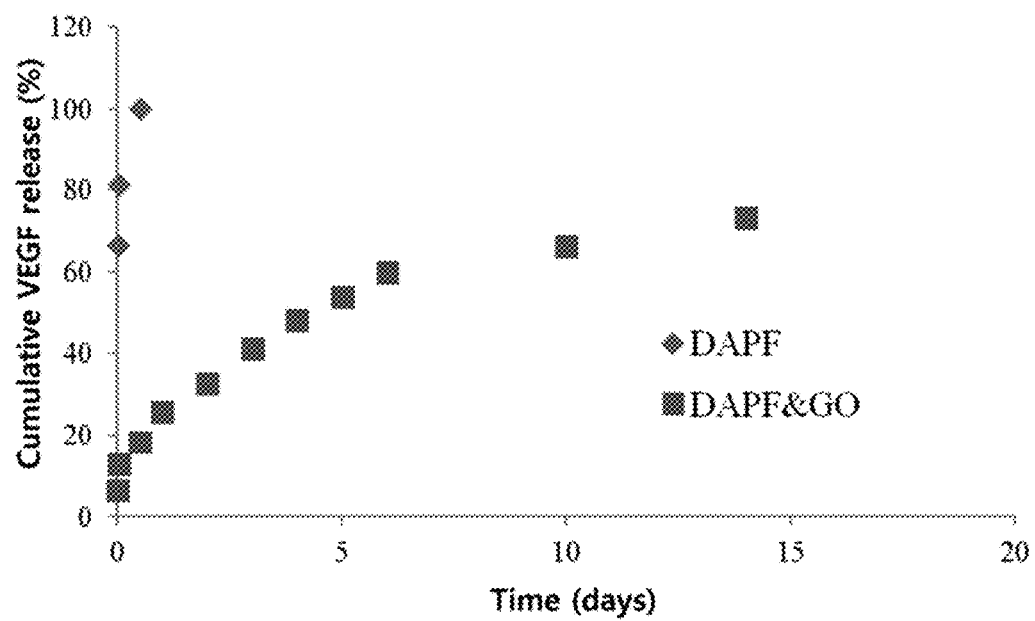
FIG. 13 shows VEGF release profiles of a hydrogel (♦) composed of 17% by weight of DAPF and a hydrogel (■) composed of DAPF and 0.1% by weight of carboxylated GO-COOH in PBS containing 2 mM sodium azidein a shaking incubator at 37° C. and 100 rpm.
Figure 14:
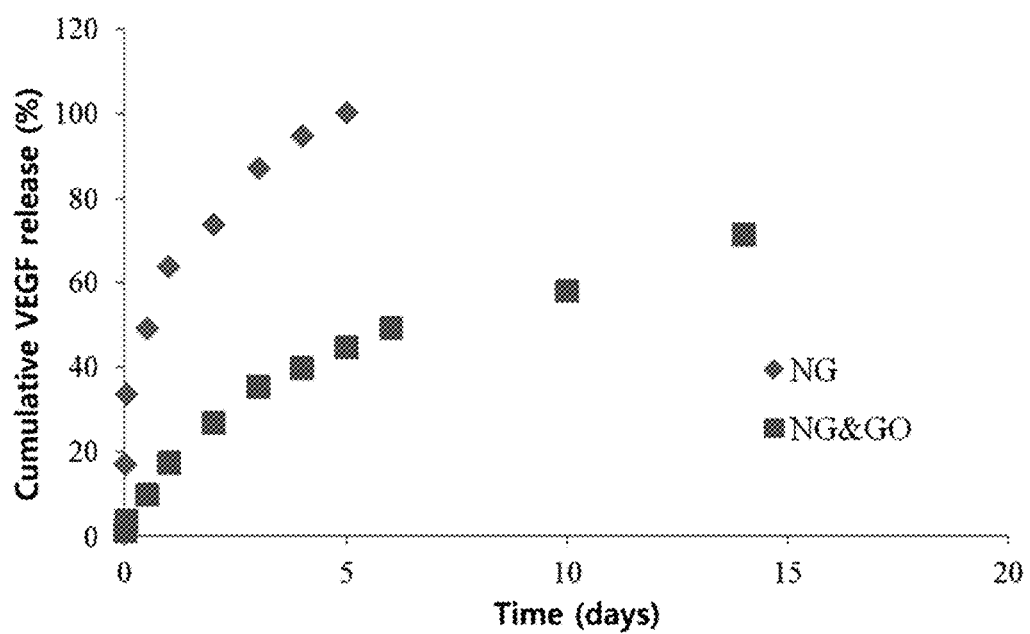
FIG. 14 shows VEGF release profiles of a hydrogel (♦) composed of 11% by weight of NG and a hydrogel (■) composed of NG and 0.1% by weight of carboxylated GO-COOH in PBS containing 2 mM sodium azidein a shaking incubator at 37° C. and 100 rpm.
Figure 15:
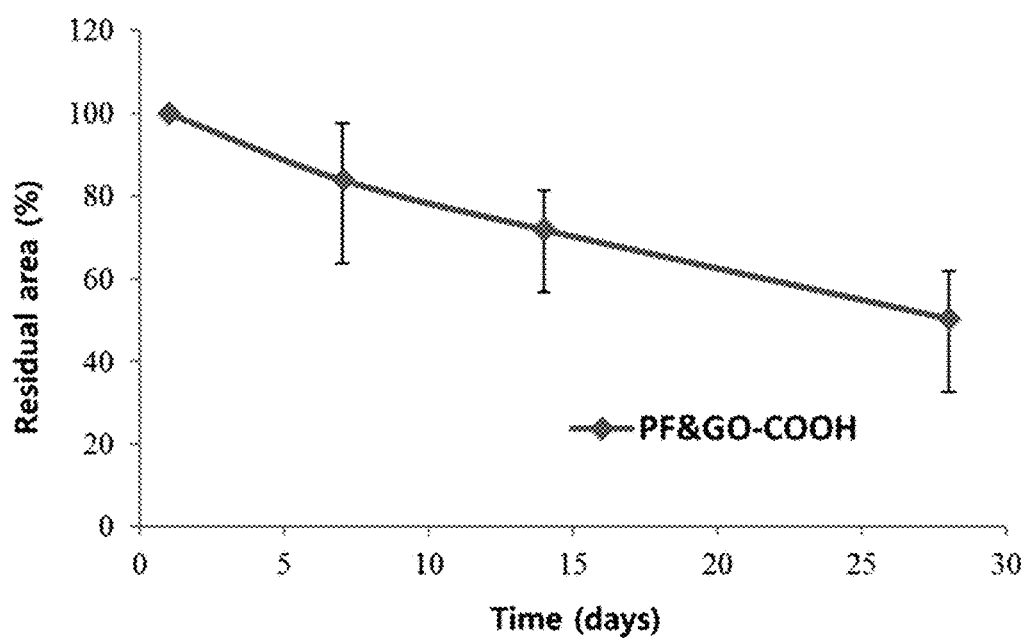
FIG. 15 is a graph showing the in vivo degradation of hydrogels (n=3) composed of 17% by weight of PF and 0.1% by weight of GO-COOH.
Figure 16:
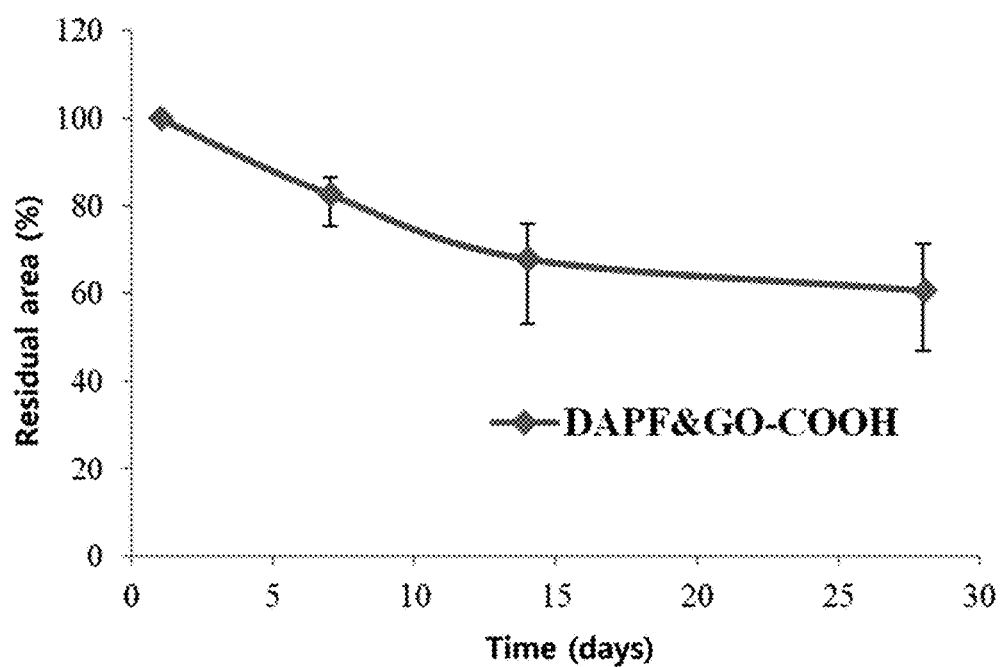
FIG. 16 is a graph showing the in vivo degradation of hydrogels (n=3) composed of 17% by weight of DAPF and 0.1% by weight of GO-COOH.
Figure 17:
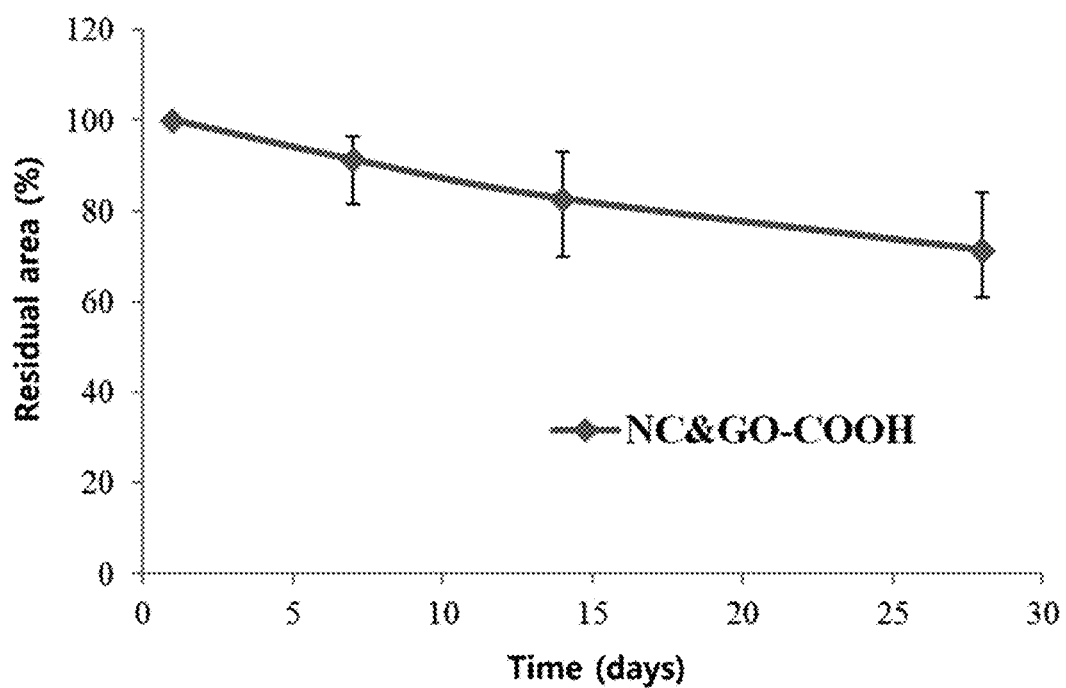
FIG. 17 is a graph showing the in vivo degradation of hydrogels(n=3) composed of 11% by weight of NG and 0.1% by weight of GO-COOH.

VEGF release profiles of the various hydrogels are shown in FIGS. 12, 13, and 14. FIG. 12 shows that VEGF was more slowly released from the PF hydrogel containing GO-COOH than from the PF hydrogel containing no GO-COOH. VEGF was almost completely released from the PF hydrogel containing no GO-COOH within one day. The degradation rates and release rates of VEGF were almost the same for the PF hydrogels; the PF hydrogel containing no GO-COOH was degraded within one day while the PF hydrogel containing GO-COOH was degraded very slowly. The results of the DAPF hydrogels were similar to those of the PF hydrogels. VEGF was completely released from the DAPF hydrogel containing no GO-COOH within one day but was more sustainedly released from the DAPF hydrogel containing GO-COOH than from the DAPF hydrogel containing no GO-COOH. The release of VEGF from the NG hydrogels was more sustained than that from the PF or DAPF hydrogels, because the NG possesses chemical crosslinking bonds. These results are in good agreement with the degradation rates of the hydrogels. As shown in FIG. 14, the NG hydrogel containing GO-COOH showed more sustained release of VEGF than the NG hydrogel containing no GO-COOH. By the GO addition, the interaction between the Pluronic-based hydrogels and GO contributed to sustained release of VEGF. That is, by the GO addition, VEGF was released more slowly from the GO-containing hydrogels than from the pure hydrogels.

These results show the effects of GO on sustained release from the hydrogels. In all cases, the lower release rates of VEGF from the GO-containing hydrogels indicate that these novel gel systems are very promising candidates as growth factor delivery systems.

Invivo Stability of the Hydrogels

To demonstrate improved in vivo stability of the GO-containing Pluronic hydrogels, each of the PF, DAPF, and NG hydrogels was subcutaneously injected into the back of mice. Each hydrogel was injected in a sol state at low temperature because it exhibits thermosensitivity. The sol state was converted into a gel state within 3 minutes after injection into the mice. In order to monitor the in vivo stability of the hydrogel, the skins of the mice after injection were cut into pieces at different time points: 1day, 1week, 2 weeks, and 4 weeks after injection, and the size of the hydrogel was monitored.

The pure PF and DAPF hydrogels were degraded within one day, which corresponded to the in vitro degradation rates. However, the PF gel containing GO-COOH was degraded very slowly; 84% of the hydrogel remained even at 7 days post-injection and 62% remained even at 28 days post-injection (FIG. 12). The DAPF gel containing GO-COOH was very slowly degraded compared to the PF gel containing GO-COOH and the in vivo degradation rate of the DAPF gel was similar to the in vitro degradation rate; 71% of the hydrogel remained even at 28 days post-injection (FIG. 13). The pure NG hydrogel was degraded within 7 days but the gel containing GO-COOH was degraded very slowly (FIG. 14); 92% of the NG hydrogel containing GO-COOH remained at 7 days post-injection and was stably present at 28 days post-injection. In all cases, the in vivo degradation rates of the hydrogels were lower than the in vitro degradation rates, presumably due to insufficient stirring and limited supply of physiological fluids under in vivo conditions compared to under in vitro experimental conditions.

In conclusion, the addition of a small amount of GO-COOH could effectively overcome in vitro and in vivo instability of physical hydrogels based on Pluronics, which has hampered the practical biomedical application of Pluronic-based hydrogels.

In vivo Biocompatibility

Figure 18:
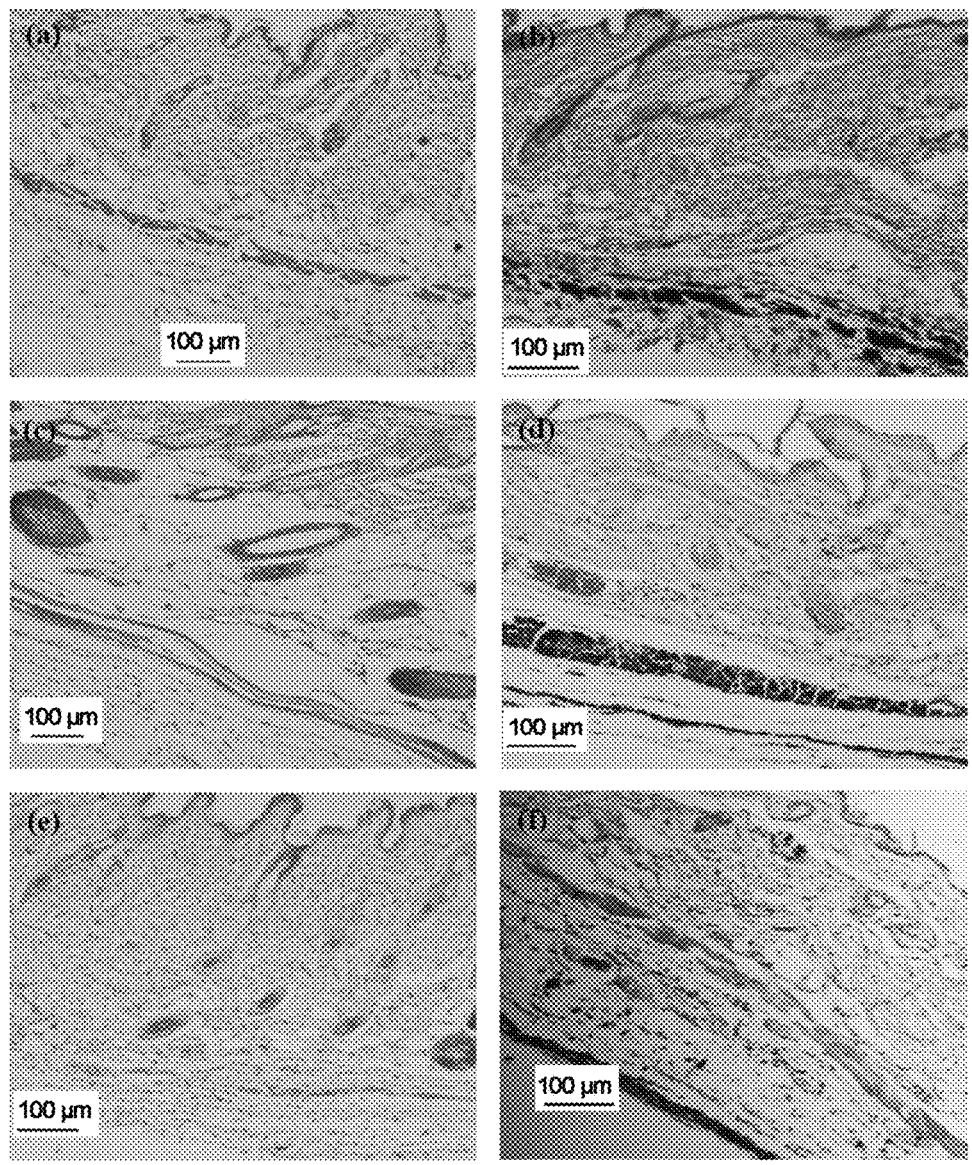
FIG. 18 shows images of H&E stained skins obtained from mice at 3 weeks post-injection with (a) PF, (b) PFGO, (c) DAPF, (d) DAPFGO, (e) NG, and (f) NGGO.

In addition to improved in vivo stability, there is a need to characterize the biocompatibility of the hydrogels for biomedical applications. The stability and toxicity problems of graphene materials remain completely unsolved. However, the stability of the composition according to the present invention was improved by the addition of a very small amount of GO-COOH. 3 weeks after injection with the pure hydrogels and the gels containing GO-COOH, immunohistological images were obtained from the injection sites (FIG. 18). The PF, DAPF, and NG hydrogels were already completely degraded and no traces of the polymers were found. For the gels containing GO-COOH, black stains were observed due to the presence of GO-COOH. In all hydrogels containing GO-COOH, however, no intensive localization of macrophages was observed. As a result of H&E staining, no noticeable inflammatory responses and symptoms were observed. Therefore, the gels containing GO-COOH showed no serious in vivo biocompatibility problems, demonstrating non-toxicity and high biocompatibility of the composition according to the present invention.

What is claimed is:

1. A composition for forming an injectable hydrogel, comprising
    0.04% to about 0.9% by weight of a graphene-based material, wherein the graphene-based material comprises graphene oxide modified by substituting surface hydroxyl groups thereof with carboxyl groups; and
    5% by weight or more of a triblock copolymer, wherein
        (i) the triblock copolymer is a copolymer represented by Formula 1:

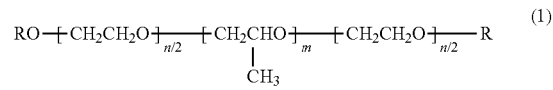

(1)

wherein n is an integer from 8 to 540, m is an integer from 16 to 70, and R is H or a vinylcarbonyl group ($CH_2$=CHCO—), or
        (ii) the triblock copolymer is the copolymer of Formula 1 wherein R is a vinylcarbonyl group and is cross-linked through the vinylcarbonyl group to form a nanogel,
    wherein a weight ratio of the graphene-based material to the triblock copolymer ranges from 0.04:17 to 0.1:17 when the triblock copolymer is the copolymer of (i), and
    wherein the weight ratio of the graphene-based material and the triblock copolymer ranges from 0.04:11 to 0.1:11 when the triblock copolymer is the crosslinked nanogel of (ii).

2. The composition according to claim 1, wherein, in Formula 1, R is H, n/2 is 100, and m is 65.

3. The composition according to claim 1, wherein, in Formula 1, R is a vinylcarbonyl group, n/2 is 100, and m is 65.

4. The composition according to claim 1, wherein the graphene-based material and the triblock copolymer are present in amounts ranging from 0.04% to about 0.9% by weight and 5 to 50% by weight, respectively.

5. The composition according to claim 1, wherein the composition comprises at least one solvent selected from the group consisting of distilled water, buffers, and physiological saline.

6. A sustained-release drug carrier comprising (1) the composition according to claims 1 and (2) a protein drug.

7. The sustained-release drug carrier according to claim 6, wherein the protein drug is a growth factor.

8. The composition according to claim 1, wherein the graphene-based material comprises graphene oxide modified by substituting all surface hydroxyl groups thereof with carboxyl groups.

* * * * *